(12) United States Patent
Steller et al.

(10) Patent No.: US 12,351,861 B2
(45) Date of Patent: Jul. 8, 2025

(54) CROSS-CONTAMINATION CONTROL

(71) Applicant: EUROIMMUN Medizinische Labordiagnostika AG, Luebeck (DE)

(72) Inventors: Ulf Steller, Buchholz (DE); Susanne Zieseniss, Gross Groenau (DE); Jenny Voss, Tangstedt (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 468 days.

(21) Appl. No.: 17/804,025

(22) Filed: May 25, 2022

(65) Prior Publication Data
US 2022/0380836 A1 Dec. 1, 2022

(30) Foreign Application Priority Data
May 27, 2021 (EP) .................................... 21176327

(51) Int. Cl.
*C12Q 1/6832* (2018.01)

(52) U.S. Cl.
CPC ................................. *C12Q 1/6832* (2013.01)

(58) Field of Classification Search
CPC ................ C12Q 1/6813; C12Q 1/6848; C12Q 2545/101
See application file for complete search history.

(56) References Cited

U.S. PATENT DOCUMENTS

2014/0093865 A1   4/2014   Espinosa et al.

FOREIGN PATENT DOCUMENTS

| WO | 2009/137055 | 11/2009 | |
| WO | 2016/187160 | 11/2016 | |
| WO | WO-2016187160 A1 * | 11/2016 | ............ B01L 3/5023 |

* cited by examiner

*Primary Examiner* — Young J Kim
(74) *Attorney, Agent, or Firm* — Grüneberg and Myers PLLC

(57) ABSTRACT

A nucleic acid or peptide detection system that includes a carrier with at least two areas is provided. A method and kit that use and/or include the nucleic acid peptide detection system are also provided.

14 Claims, 7 Drawing Sheets

Fig. 5

| Spot | Field A (pos. sample) | Field B (neg. sample) | Field C (pos. sample) | Field D (neg. sample) | Definition of positive and negative signals |
|---|---|---|---|---|---|
| Fate | no cross-cont. | cross-cont. with sample solution of Field A | no cross-cont. | cross-cont. with sample solution of Field C | |
| B27_Ex2 | 46254 | 2353 | 34800 | 2695 | < 1500: negative 1500-3000: unclear > 3000: positive |
| B27_Ex2 | 46585 | 2320 | 37127 | 2385 | |
| B27_Ex2 | 47216 | 2413 | 35487 | 3051 | |
| B27_Ex2 | 46952 | 2284 | 34032 | 2716 | |
| B27_Ex3 | 31224 | 1598 | 20702 | 1723 | < 1200: negative 1200-2000: unclear > 2000: positive |
| B27_Ex3 | 30437 | 1545 | 19698 | 1452 | |
| B27_Ex3 | 35611 | 1621 | 24044 | 2063 | |
| B27_Ex3 | 31276 | 1532 | 19241 | 1719 | |
| CC-I | 48197 | 12955 | 48897 | 34717 | > 500: positive |
| CC-I | 48422 | 12221 | 48744 | 32565 | |
| CC-II | 0 | 49082 | 0 | 49275 | |
| CC-II | 0 | 49064 | 0 | 49149 | |

Fig. 6

| Spot | Field A (pos. sample) | Field B (neg. sample) | Field C (pos. sample) | Field D (neg. sample) | Definition of positive and negative signals |
|---|---|---|---|---|---|
| Fate | no cross-cont. | cross-cont. with washing buffer of Field A | no cross-cont. | cross-cont. with washing buffer of Field C | |
| B27_Ex2 | 43544 | 12 | 39897 | 65 | < 1500: negative<br>1500-3000: unclear<br>> 3000: positive |
| B27_Ex2 | 42877 | 51 | 39241 | 0 | |
| B27_Ex2 | 45612 | 7 | 41401 | 78 | |
| B27_Ex2 | 43519 | 41 | 40463 | 50 | |
| B27_Ex3 | 25211 | 0 | 25274 | 0 | < 1200: negative<br>1200-2000: unclear<br>> 2000: positive |
| B27_Ex3 | 26066 | 52 | 22535 | 0 | |
| B27_Ex3 | 26351 | 0 | 25151 | 0 | |
| B27_Ex3 | 25613 | 0 | 23435 | 0 | |
| CC-I | 48138 | 1088 | 48980 | 2899 | > 500: positive |
| CC-I | 47794 | 1306 | 48682 | 2618 | |
| CC-II | 0 | 49146 | 0 | 49330 | |
| CC-II | 0 | 49041 | 17 | 49153 | |

CROSS-CONTAMINATION CONTROL

CROSS REFERENCE TO RELATED APPLICATION

This application claims the benefit of priority to European Application No. EP 21176327.1, filed on May 27, 2021. The content of this application is hereby incorporated by reference in its entirety.

BACKGROUND OF THE INVENTION

Field of the Invention

The present invention relates to a nucleic acid or peptide detection system (1) comprising a carrier (2) with at least two areas (3, 4). Further the present invention relates to methods comprising the nucleic acid or peptide detection system (1) of the invention and to a kit (13).

Description of the Related Art

Microarrays are detection systems for DNA and proteins which allow studying the interaction of said biological molecules in multiple parallel reactions on a microplate. For this reason nucleic acid and protein microarrays are not only used in laboratory research but are also part of the routine diagnostic equipment for a variety of diseases, such as infectious diseases, autoimmune diseases, cancer, allergies, neurological diseases, food intolerances and metabolic diseases. In detail, a microarray can be regarded as a multiplex lab-on-a-chip which is a two-dimensional array on a solid substrate—usually a glass slide or silicon thin-film cell—that assays large amounts of biological material using high-throughput screening miniaturized, multiplexed and parallel processing and detection methods. The concept and methodology of microarrays was first introduced and illustrated in antibody microarrays, whereas the nucleic acid microarrays and its corresponding industry started to grow significantly in 1995.

As multi-sector arrays are contacted with samples originating from different patients cross-contamination may occur between the samples during the time that they are in contact with the array regardless how much care is taken to avoid such cross-contamination. Sample cross-contamination causes that fluids (especially probes) of an unrelated areas/well are mixed with reagents of another area/well. As a consequence, the data obtained from the area/well which contains the mixed substances may be of inferior quality and may not be reliable.

As such, devices and methods of detecting cross-contamination between samples applied on a multi-sector array are needed. This problem is solved by the devices and methods of the present invention.

SUMMARY OF THE INVENTION

The present inventors have developed a nucleic acid or peptide detection system containing a cross-contamination control which is based on different single-stranded acceptor control nucleic acids and different labelled single-stranded donor control nucleic acids, which are non-covalently attached to a carrier, such as a glass slide. Neighboring areas of a glass slide alternatingly comprise one of two different donor control nucleic acids and one of two different acceptor control nucleic acids. The acceptor control nucleic acid and the donor control nucleic acid of alternating areas can bind to each other. Thus, the donor control nucleic acids will be solved after coming into contact with a liquid sample or a buffer comprising the sample. After the samples are applied on the detection system of the present invention, each area comprises an acceptor control nucleic acid stably attached, e.g. covalently or by polycationic binding, to the carrier and a solved donor control nucleic acid. If no cross-contamination occurs, the donor control nucleic acid will be washed out and no signal can be detected. However, in case of a cross-contamination the solved donor control nucleic acid comes into contact with an acceptor control nucleic acid of the neighbor area and both will bind to each other. Even after washing steps the label of the donor control nucleic acid can be detected. FIGS. 1B and 3 show a preferred embodiment, wherein the area comprises both acceptor control nucleic acids. The matching donor and acceptor control nucleic acid pair contained within the same area can be used as an internal area control.

The reversible attachment of the donor control nucleic acid to the carrier material of the detection system can easily be achieved by drying a solution containing the donor control nucleic acid on the carrier.

Surprisingly, the detection system of the invention is not only be capable to detect cross-contamination directly after adding the sample or during incubation but can also detect cross-contamination occurring during subsequent washing steps.

Therefore, the present inventors have created a highly efficient cross-contamination control system which can be applied on microplates using standard equipment.

Thus, in a first aspect the present invention is directed to a nucleic acid or peptide detection system (1) comprising a carrier (2) with at least two areas (3, 4),
  wherein a first area (3) comprises
    single-stranded nucleic acids (5) covalently attached to the carrier (2) for detection of nucleic acids of interest or peptides (6) covalently attached to the carrier (2) for detection of peptides of interest;
    a first single-stranded acceptor control nucleic acid (7) covalently attached or attached by polycationic binding to the carrier (2); and
    a first single-stranded donor control nucleic acid (8) non-covalently attached to the carrier (2) and comprising a detectable label;
  wherein a second area (4) comprises
    single-stranded nucleic acids (5) covalently attached to the carrier (2) for detection of nucleic acids of interest or peptides (6) covalently attached to the carrier (2) for detection of peptides of interest;
    a second single-stranded acceptor control nucleic acid (9) covalently attached or attached by polycationic binding to the carrier (2); and
    a second single-stranded donor control nucleic acid (10) non-covalently attached to the carrier (2) and comprising a detectable label;
  wherein the second donor control nucleic acid (10) is able to hybridize under suitable conditions with the first acceptor control nucleic acid (7) and
  the first donor control nucleic acid (8) is able to hybridize under suitable conditions with the second acceptor control nucleic acid (9).

In preferred embodiments of the nucleic acid or peptide detection system (1) of the invention, the first area (3) additionally comprises the second single-stranded acceptor control nucleic acid (9) covalently attached or attached by polycationic binding to the carrier (2) and the second area (4) additionally comprises the first single-stranded acceptor control nucleic acid (7) covalently attached or attached by polycationic binding to the carrier (2).

In preferred embodiments of the nucleic acid or peptide detection system (1) of the invention,
(a) the single-stranded nucleic acids (5) and the acceptor control nucleic acids (7, 9) are spatially separated;
(b) the peptides (6) and the acceptor control nucleic acids (7, 9) are spatially separated; and/or
(c) the first single-stranded acceptor control nucleic acid (7) and the second single-stranded acceptor control nucleic acid (9) in each area (3, 4) are spatially separated.

In preferred alternative embodiments, the donor control nucleic acid (8, 10) is dried up on the carrier (2).

Further, in preferred embodiments,
(a) the first single-stranded acceptor control nucleic acid (7) is at least 80% complementary to the second single-stranded donor control nucleic acid (10) over a stretch of at least 10 nucleotides; and/or
(b) the second single-stranded acceptor control nucleic acid (9) is at least 80% complementary to the first single-stranded donor control nucleic acid (8) over a stretch of at least 10 nucleotides.

In additionally preferred embodiments, the carrier (2) comprises a plurality of areas (3, 4) that are arranged to form at least one row. In even more preferred embodiments, the plurality of areas (3, 4) alternatingly comprise (i) the first acceptor control nucleic acid (7) and the first donor control nucleic acid (8) and (ii) the second acceptor control nucleic acid (9) and the second donor control nucleic acid (10).

In preferred embodiments, the detection label of the donor control nucleic acid (8, 10) is a dye, preferably a fluorescent dye. In more preferred alternatives of this embodiment, the dye is selected from the group consisting of cyanine derivatives, e.g. cyanine 3 and cyanine 5, fluorescein, fluorescein isothiocyanate (FITC), 6-FAM phosphoramidite, 6-JOE, rhodamines, 5-TAMRA, ROX and Texas Red. Further dyes include xanthene derivatives, such as fluorescein, rhodamine, Oregon green, eosin, and Texas red; cyanine derivatives, such as cyanine, indocarbocyanine, oxacarbocyanine, thiacarbocyanine, and merocyanine: squaraine derivatives and ring-substituted squaraines, including Seta and Square dyes; squaraine rotaxane derivatives, comparable to Tau dyes; naphthalene derivatives, such as dansyl and prodan derivatives; coumarin derivatives; oxadiazole derivatives, such as pyridyloxazole, nitrobenzoxadiazole and benzoxadiazole; anthracene derivatives, such as anthraquinones, including DRAQ5, DRAQ7 and CyTRAK Orange; pyrene derivatives, such as cascade blue, etc.; oxazine derivatives, such as Nile red, Nile blue, cresyl violet, oxazine 170, etc.; acridine derivatives, such as proflavin, acridine orange, acridine yellow, etc.; arylmethine derivatives, such as auramine, crystal violet, malachite green; tetrapyrrole derivatives, such as porphin, phthalocyanine, bilirubin; and dipyrromethene derivatives, such as BODIPY, aza-BODIPY.

In preferred embodiments of the present invention, each of the single-stranded nucleic acids (5), the acceptor control nucleic acid (7, 9) and the donor control nucleic acid (8, 10) has a length of 10 to 100 nucleotides, preferably 10 to 50 nucleotides.

Moreover, in preferred embodiments the carrier (2) material is plastic, glass, silicon, ceramic or metal.

In a second aspect, the present invention is directed to a kit (13) comprising
(I) a nucleic acid or protein verification system comprising a carrier (2) with at least two areas (3, 4),
wherein a first area (3) comprises
single-stranded nucleic acids (5) covalently attached to the carrier (2) for detection of nucleic acids of interest or peptides (6) covalently attached to the carrier (2) for detection of peptides of interest;
a first single-stranded acceptor control nucleic acid (7) covalently attached or attached by polycationic binding to the carrier (2); and
wherein a second area (4) comprises
single-stranded nucleic acids (5) covalently attached to the carrier (2) for detection of nucleic acids of interest or peptides (6) covalently attached to the carrier (2) for detection of peptides of interest;
a second single-stranded acceptor control nucleic acid (9) covalently attached or attached by polycationic binding to the carrier (2); and
(II) a first single-stranded donor control nucleic acid (14) comprising a detectable label and a second single-stranded donor control nucleic acid (15) comprising a detectable label,
wherein the second donor control nucleic acid (15) is able to hybridize under suitable conditions with the first acceptor control nucleic acid (7) and
the first donor control nucleic acid (14) is able to hybridize under suitable conditions with the second acceptor control nucleic acid (9).

In a preferred embodiment, the first and the second donor control nucleic acids (14, 15) are separately and non-covalently attached to sample tubes.

In a third aspect, the present invention is directed to a method for detecting a nucleic acid or a peptide for interest comprising contacting the nucleic acid or peptide of interest with the nucleic acid or peptide detection system (1) of the present invention or with the nucleic acid or peptide verification system (12) and the first and second donor control nucleic acids (14, 15) of the invention.

BRIEF DESCRIPTION OF THE DRAWINGS

FIG. 1A shows the detection system of the invention. Each area comprises one donor control nucleic acid and acceptor control nucleic acids whereas

FIG. 3 is based on a preferred embodiment of the invention, wherein each area contains one donor control nucleic acid and two acceptor control nucleic acids. The cross-contamination of the second area is indicated by the presence of two donor control nucleic acid signals.

FIG. 5 shows the results of nucleic acid detection using the detection system of the present invention. The results comprise non-contaminated controls and cross-contamination occurring during the application of the solution comprising the amplified HLA-B exons. Cells in grey indicate signals considered an invalid overall test result due to cross-contamination bold numbers indicate positive signals. B27_Ex2 and B27_Ex3 indicate the results for microarray detection of exon 2 and exon 3 of the gene HLA-B. CC-I indicates the result obtained from the first acceptor control nucleic acid. CC-II indicates the result obtained from the second acceptor control nucleic acid FIG. 6 shows the results of nucleic acid detection using the detection system of the present invention. The results comprise non-contaminated controls and cross-contamination occurring during a washing step after the solution comprising the nucleic acid of interest was already applied on the detection system. Cells in grey indicate signals considered an invalid overall test result due to cross-contamination. Bold numbers indicate positive signals. B27_Ex2 and B27_Ex3 indicate the results for microarray detection of exon 2 and exon 3 of the gene HLA-B. CC-I indicates the result obtained from the first acceptor control nucleic acid. CC-II indicates the result obtained from the second acceptor control nucleic acid

Figure 1A:
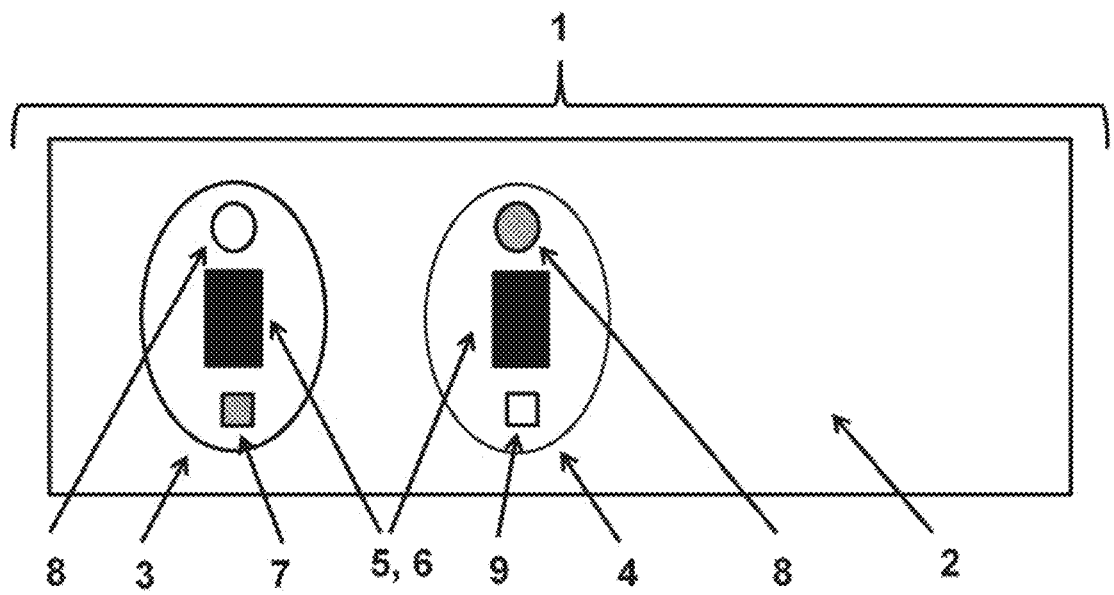

The present invention is based on the inventors' surprising finding that labelled nucleic acids which are non-covalently attached to a carrier (preferably the nucleic acids are dried up on the carrier) can form the basis of a cross-contamination system. Alternating areas of a glass slide contain two different versions of the single-stranded dried up nucleic acids, which are called donor control nucleic acids. After being dissolved a donor control nucleic acid can bind to a single-stranded acceptor control nucleic acid that is located in a neighboring area. As the donator and acceptor control nucleic acids of neighboring areas came only into contacting after cross-contamination, the above described system allows the detection of fluids that are mistakenly transferred from one area to a neighboring area.

According to the present invention, the term "nucleic acid", as used herein, refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. Thus, the terms nucleoside, nucleotide, deoxynucleoside and deoxynucleotide generally include analogs.

Typically a nucleic acid will comprise phosphodiester bonds, however, nucleic acids may comprise a modified backbone comprising, for example, phosphoramide, phosphorothioate, phosphorodithioate, O-methylphophoroamidite linkages, and peptide nucleic acid backbones and linkages. Other analog nucleic acids include those with positive backbones; non-ionic backbones and non-ribose backbones. Nucleic acids containing one or more carbocyclic sugars are also included within the definition of nucleic acids. These modifications of the ribose-phosphate backbone may be done to facilitate the addition of electron transfer moieties, or to increase the stability and half-life of such molecules in solution. In addition, mixtures of naturally occurring nucleic acids and analogs can be made.

Peptide nucleic acids (PNA) which includes peptide nucleic acid analogs can be used in the methods and compositions of the invention. Such peptide nucleic acids have increased stability. These backbones are substantially non-ionic under neutral conditions, in contrast to the highly charged phosphodiester backbone of naturally occurring nucleic acids.

Nucleic acids of the invention comprise single as well as double-stranded nucleic acids. "Single-stranded", as used herein, refers to a nucleic acid molecule wherein all the nucleotide bases are connected to one another by covalent bonds and wherein the bases do not hybridize to a substantially complementary nucleic acid. However, the single-stranded nucleic acid may hybridize with a substantially complementary nucleic acid at a later stage to become a double-stranded molecule. As used herein, the term "substantially complementary" is used to indicate a sufficient degree of complementarity or precise pairing such that stable and specific binding occurs between two nucleic sequences. It is understood in the art that the sequence of a nucleic acid need not be 100% complementary to that of its target. The term encompasses a sequence complementary to another sequence with the exception of an overhang. In some cases, the sequence is complementary to the other sequence with the exception of 1-2 mismatches. In some cases, the sequences are complementary except for 1 mismatch. In some cases, the sequences are complementary except for 2 mismatches. In other cases, the sequences are complementary except for 3 mismatches.

In preferred embodiments, the detection system of the present invention detects nucleic acid molecules.

The term "peptide", as used herein, refers to a sequence of amino acids made up of a single chain of amino acids joined by peptide bonds. Generally, the term "peptide" used in the sense of the present invention also includes "polypeptides", "proteins" and "modified peptides". A "modified peptide" may include the incorporation of non-natural amino acids into the peptides covalently attached to the carrier, including synthetic non-native amino acids, substituted amino acids, or one or more D-amino acids. Such incorporation is desirable in certain situations. D-amino acid-containing peptides exhibit increased stability in vitro compared to L-amino acid-containing forms. More specifically, D-peptides are resistant to endogenous peptidases and proteases. In a preferred embodiment, the peptides may comprise chemical modifications, for example isotopic labels or covalent modifications such as glycosylation, phosphorylation, acetylation, decarboxylation, citrullination, hydroxylation and the like. The person skilled in the art is familiar with methods for the modification of polypeptides.

The term "polypeptide", as used herein, refers to a compound made up of at least 50 amino acid residues linked by peptide bonds. The term "protein", as used herein, may be synonymous with the term "polypeptide" or may refer, in addition, to a complex of two or more polypeptides.

"Detection system", as used herein, refers to the components used to detect a biological analyte and may include enzymes, enzyme substrates, binding partners (e.g. antibodies or receptors), labels, dyes, and instruments for detecting light absorbance or reflectance, fluorescence, and/or luminescence (e.g. bioluminescence or chemiluminescence). In preferred embodiments, the detection system is selected from the group consisting of nucleic acid and protein arrays, more preferably nucleic acid and protein microarrays. In even more preferred embodiments, the detection is a nucleic acid detection system, such as a DNA microarray or DNA chip, as interchangeably used herein.

A DNA microarray, also known as DNA chip or biochip, is a collection of microscopic DNA spots attached to a solid surface/carrier. DNA microarrays are used e.g. to measure the expression levels of large numbers of genes simultaneously, to genotype multiple regions of a genome or to detect nucleic acids of pathogens. Each DNA spot contains picomoles (10-12 moles) of a specific DNA sequence, known as probes (or reporters). These can be a short section of a gene or other DNA element that are used to hybridize a DNA or RNA sample under high-stringency conditions. Probe-target hybridization is usually detected and quantified by detection of fluorophore-, silver-, or chemiluminescence-labeled targets to determine relative abundance of nucleic acid sequences in the target. Stringency of hybridization reactions is readily determinable by one of ordinary skilled in the art, and in general is an empirical calculation dependent on nucleic acid lengths, reaction temperature and salt concentration. The term "hybridize (under suitable conditions)", as used herein, refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al.). High stringency hybridization conditions as for instance described in Sambrook et al. are particularly preferred. Particularly preferred stringent hybridization conditions are for instance present if hybridization and washing occur at 65° C. as indicated above. Non-stringent hybridization conditions for instance with hybridization and washing carried out at 45° C. and are less preferred and at 35° C. even less.

Further, in preferred embodiments, the first single-stranded acceptor control nucleic acid is at least 80% complementary to the second single-stranded donor control nucleic acid over a stretch of at least 10 nucleotides; and/or the second single-stranded acceptor control nucleic acid is at least 80% complementary to the first single-stranded donor control nucleic acid over a stretch of at least 10 nucleotides. In more preferred embodiments, the donor and acceptor control nucleic acids are complementary over a length of at least 15, at least 20, at least 25, at least 30 or at least 35 nucleotides. Alternatively or in addition, in preferred embodiments the stretch of complementary nucleotides between the donor and acceptor control nucleic acids has at least 85%, at least 90%, at least 93%, at least 95%, at least 97%, at least 98%, at least 99% or 100% complementary nucleotides. The complementary stretch can comprise the whole sequence of the donor or acceptor control nucleic acid or can only comprise a partial segment of such sequences.

The term "carrier", as used herein, refers to a material or group of materials having a rigid, semi-rigid or solid surface or surfaces that allows the covalent or polycationic attachment of nucleic acids and proteins as well as the non-covalent attachment of nucleic acids. The carrier is formed to comprise at least two areas, which may be flat, or wholes or wells. Preferred carrier materials are plastic, glass and metal. Alternatively, the carrier may be a bead, preferably a paramagnetic bead, a test strip, a microtiter plate, a microarray, a blot and a membrane, preferably a line blot. In preferred embodiments of the invention, the carrier is a plastic microplate as well-known by the person skilled in the art. In preferred embodiments, the carrier is selected from the group consisting of a 6-well, 12-well, 24-well, 48-well, 96-well, 384-well, 1536-well and 3456-well (micro)plate. In still more preferred embodiments, the carrier is a 96-well microplate. However, in preferred embodiments, the carrier is a glass or plastic slide.

According to the present invention, an acceptor control nucleic acid is a single-stranded nucleic acid molecule covalently attached or attached by polycationic binding to the carrier. Preferably, the acceptor control nucleic acid is covalently attached to the carrier. The acceptor control nucleic acid may comprise any sequence that allows specific hybridization to the donor control nucleic acid molecule. These two sequences can hybridize over their full sequence length or, alternatively, can interact by hybridization of sequence segments of one or both molecules.

The donor control nucleic acid is a single-stranded nucleic acid molecule that can hybridize to the acceptor control nucleic acid. The donor control nucleic acid is reversibly attached to the carrier by a non-covalent attachment. In preferred embodiments, the donor control nucleic acid molecule can be detached from the carrier by being contacted with a fluid, more preferably a water-based fluid, such as water, a water-based buffer or a washing solution. Additionally, the donor control nucleic acid comprises a detectable label.

The terms "covalent" or "covalently", as used herein, refer to the nature of a chemical bonding interaction between atoms. A covalent bond is a chemical bonding that involves the sharing of electron pairs between atoms. The stable balance of attractive and repulsive forces between atoms when they share electrons is referred to as covalent bonding. The sharing of electrons allows each atom to attain the equivalent of a full outer shell, corresponding to a stable electronic configuration. Covalent bonding includes various kinds of interactions, e.g., σ-bonding, π-bonding, metal-to-metal bonding, agostic interactions, and three-center two-electron bonds.

The terms "non-covalent" or "non-covalently", as used herein, refer to the nature of a chemical bonding interaction between atoms. A non-covalent bond is a type of chemical bonding that does not involve the sharing of pairs of electrons, but rather involves more dispersed variations of electromagnetic interactions. There are four commonly mentioned types of non-covalent interactions: hydrogen bonds, ionic bonds, van der Waals forces, and hydrophobic interactions. In preferred embodiments of the present invention, the non-covalent bond between the carrier and the donor control nucleic acid is obtained by drying up a donor control nucleic acid on the carrier.

The term "polycationic binding", as used herein, refers to a polymer comprising a plurality of cationic groups that are able to form a binding with negatively charged nucleic acid molecules. In a preferred embodiment, the polycationic polymer is poly-L-lysine (PLL) and branched polyethylenimine (PEI). In more preferred embodiments, the polycationic polymer is poly-L-lysine (PLL).

The term "detectable label", as used herein, refers to any chemical moiety attached to a nucleotide, nucleotide polymer, or nucleic acid binding factor, wherein the attachment may be covalent or non-covalent. Preferably, the label is detectable and renders the nucleotide or nucleotide polymer detectable to the practitioner of the invention. Detectable labels that may be used in combination with the methods disclosed herein include, for example, a fluorescent label, a chemiluminescent label, a quencher, a radioactive label, biotin and gold, or combinations thereof. Detectable labels include luminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention. In preferred embodiments, the detection label of the donor control nucleic acid is a dye, preferably a fluorescent dye. In more preferred alternatives of this embodiment, the dye is selected from the group consisting of cyanine derivatives, fluorescein, fluorescein isothiocyanate (FITC), 6-FAM phosphoramidite, 6-JOE, rhodamines, 5-TAMRA, ROX and Texas Red.

The term "area", as used herein, refers to a defined zone on the carrier which includes (i) single-stranded nucleic acids (5) or peptides (6) for detection of nucleic acids or peptides of interest, (ii) the first or second single-stranded acceptor control nucleic acid (7, 9) and the first or second single-stranded donor control nucleic acid (8, 10). Preferably, the area comprises both, the first and the second acceptor control nucleic acid (7, 9). The area can be a flat space on the carrier, such as a defined space on a glass slide or a well, such as a well in a microwell plate.

"Spatially separated", as used herein, refers to distinct spots of the nucleic acid and protein molecules used to determine the interaction with a binding partner of interest and spots of the donor and acceptor control nucleic acid molecules.

In preferred embodiments, the detectable labels of the first and the second donor control nucleic acids are not identical and can be independently selected from the detectable labels as described above. Nonetheless, in alternative embodiments, the detectable labels of the first and the second donor control nucleic acids are identical and both signals can be discriminated based on their location after binding. Signals of the first donor control nucleic acid can only be located where the corresponding acceptor control nucleic acid has been spotted on the carrier, whereas signals of the second donor control nucleic acid can only be located where the corresponding acceptor control nucleic acid has been spotted on the carrier.

The term "dried up", as used herein, refers to donor control nucleic acid which is spotted in solution on the carrier. After evaporation of the solution, the donor control nucleic acid is reversibly attached to the carrier. It is noted that the evaporation process can preferably enhanced, such as by increasing the incubation temperature and/or lowering the atmospheric pressure.

Figure 4:
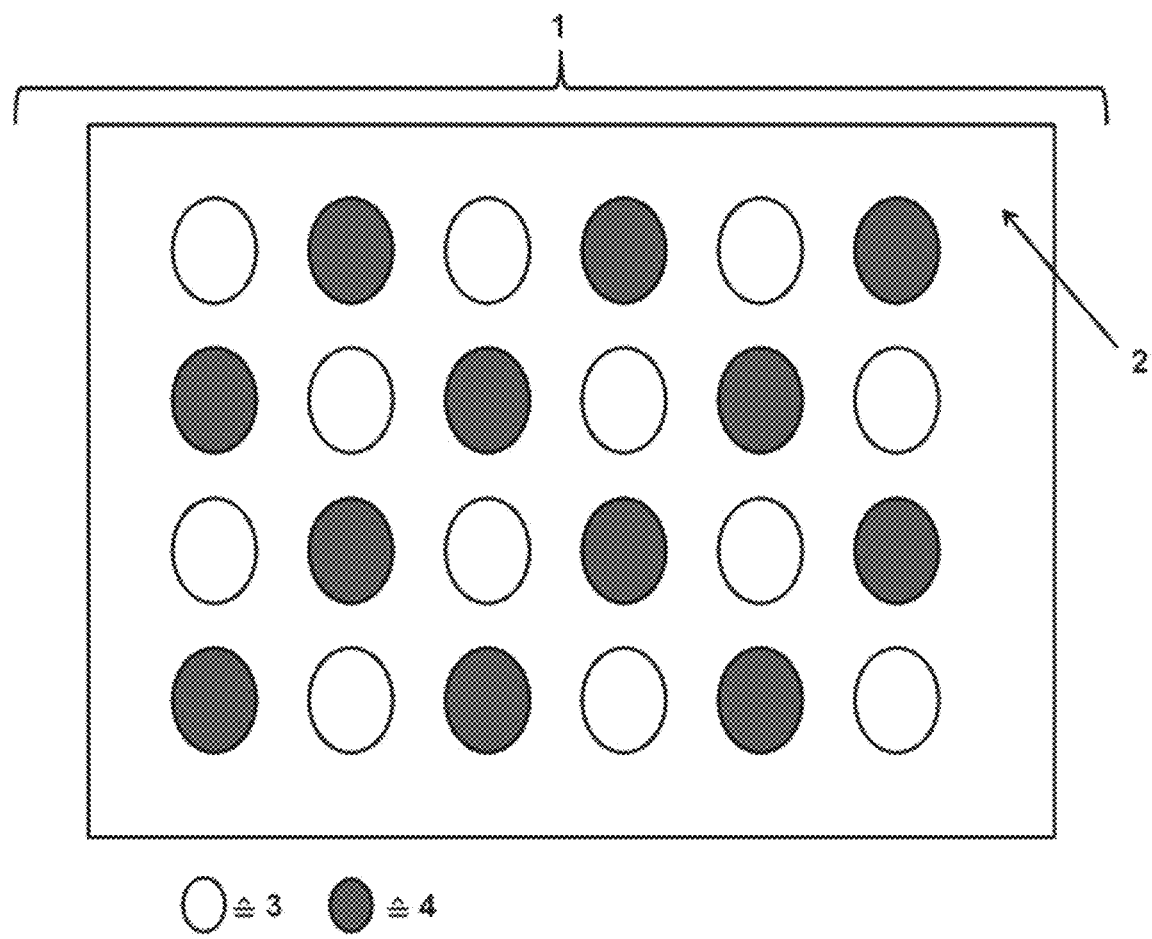
FIG. 4 shows a preferred embodiment of the present invention, wherein the areas of the detection system are arranged to form horizontal and vertical rows. The white and the grey colors of the areas indicate that they alternatingly comprise the first and the second donor control nucleic acid.

The term "arranged to form (at least) one row", as used herein, refers to arrangement of areas in the carrier. The above term means that the centers of at least three areas substantially lay on a straight line. This includes also the possibility that the areas are part of two (or even more) rows as shown in FIG. 4.

"Alternatingly", as used herein, refers to the settings of donor and acceptor control nucleic acids contained in neighboring areas. The present cross-contamination system comprises two different donor control nucleic acids as well as two different acceptor control nucleic acids. In areas of a row, the first area comprises a type A acceptor control nucleic acid, whereas the next area comprises a type B acceptor nucleic acid. This will be repeated to generate an A-B-A-B-A-B . . . row. The same setting is applied for the donor control nucleic acids. It is further noted that one area always contains only one donor control nucleic acid but may comprise one or both acceptor control nucleic acids. In case only one acceptor control nucleic acid is spotted on the areas, a matching pair of donor and acceptor control nucleic acids is "alternatingly" located in neighboring areas.

"Cyanine derivative", as used herein, refers to polymethine dyes, such as those based upon the cyanine, merocyanine, styryl and oxonol ring.

As used herein, "rhodamine" refers to a family of related dyes which are a subset of the triarylmethane dyes. They are derivatives of xanthene. Members of the rhodamine family include, but are not limited to Rhodamine 6G, Rhodamine 123, Rhodamine B and Texas Red.

The length of the donor control nucleic acid and/or the length of the acceptor control nucleic acid is preferably 10 to 100 nucleotides, more preferably the length is 11 to 90 nucleotides, 12 to 80 nucleotides, 13 to 70 nucleotides, 14 to 60 nucleotides, 15 to 50 nucleotides, 16 to 40 nucleotides, 17 to 30 nucleotides, 18 to 25 nucleotides or 19 to 20 nucleotides.

The amount of donor control nucleic acid and/or acceptor control nucleic acid applied on the carrier is preferably 500 fmol to 1000 pmol, more preferably 700 fmol to 900 pmol, 1 pmol to 800 pmol, 2 pmol to 500 pmol, 3 pmol to 200 pmol, 4 pmol to 100 pmol, 5 pmol to 70 pmol, 6 pmol to 50 pmol, 7 pmol to 30 pmol, 8 to 20 pmol, 9 pmol to 17 pmol or 10 pmol to 15 pmol.

The term "contacting", as used herein, refers to bringing at least two different compounds in physical proximity as to allow physical and/or chemical interaction of said compounds. In accordance with the method of this invention, the said two different compounds are a nucleic acid or protein obtained from a patient and the molecules spotted on the detection system of the invention. Contacting is carried out under conditions and for a time being sufficient to allow interaction of the molecules.

The term "sample", as used herein, refers to a fluid (blood, serum, urine, semen, CSF), intact cells or extracts thereof, or tissue samples. The sample may be a clinical cytology specimen (e.g., fine needle breast biopsy or pulmonary cytology specimen) or a human tissue specimen from, for example, stomach, lung, breast, ovarian, pancreatic, prostate or brain tumors. The tissue specimen may be fresh or frozen. Preferably, the sample is fluid sample.

In preferred embodiments, the terms "detecting in a sample" and/or "determining in a sample", as used herein, refer to the qualitative or quantitative measurement of a compound or molecule in said sample. In many cases detecting or detecting the presence of an DNA, optionally meaning determining whether the concentration of the DNA is beyond a certain threshold preferably as set by measurement using array technology or RT-PCR, preferably as described in the examples, in the implicit detection limit by this method, often suggested by the detection limit, in the sample, is sufficient for the diagnosis. If the DNA can be detected, this will be information instrumental for the clinician's diagnosis and indicates an increased likelihood that the patient suffers from a disease. In a preferred embodiment, the relative concentration of the DNA in the sample, compared to the level that may be found in the average healthy subject, may be determined. In a preferred embodiment, the term "detecting the presence", as used herein, means that it is sufficient to check whether a signal sufficiently beyond any background level may be detected using a suitable complex detection method that indicates that the DNA of interest is present or more DNA of interest is present than would be in a healthy subject. In a more preferred embodiment this may involve determining whether the concentration is at least 0.1, preferably 0.2, 0.5, 1, 2, 5, 10, 20, 25, 50, 100, 200, 500, 1000, 10000 or 100000 times higher than the concentration of the DNA of interest found in the average healthy subject.

It is noted that the above described definitions apply to features mentioned in the context of the nucleic acid or peptide detection system (1) of the invention, the kit (13) of the invention as well as the method of the invention.

Thus, in preferred embodiments, the donor control nucleic acids (14, 15) are dried up on the sample tube. In other preferred embodiments, the detection label of the donor control nucleic acids (14, 15) is a dye, more preferably a fluorescent dye. In even more preferred alternatives of this embodiment, the dye is selected from the group consisting of cyanine derivatives, fluorescein, fluorescein isothiocyanate (FITC), 6-FAM phosphoramidite, 6-JOE, rhodamines, 5-TAMRA, ROX and Texas Red. In preferred alternative embodiments of the present invention, each of the single-stranded donor control nucleic acid (14, 15) has a length of 10 to 100 nucleotides, preferably 10 to 50 nucleotides.

The present invention is further illustrated by the following examples, sequences and figures from which further features, embodiments, aspects and advantages of the present invention may be taken. All methods and materials similar or equivalent to those described herein can be used in the practice or testing of the present invention, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

Figure 1B:
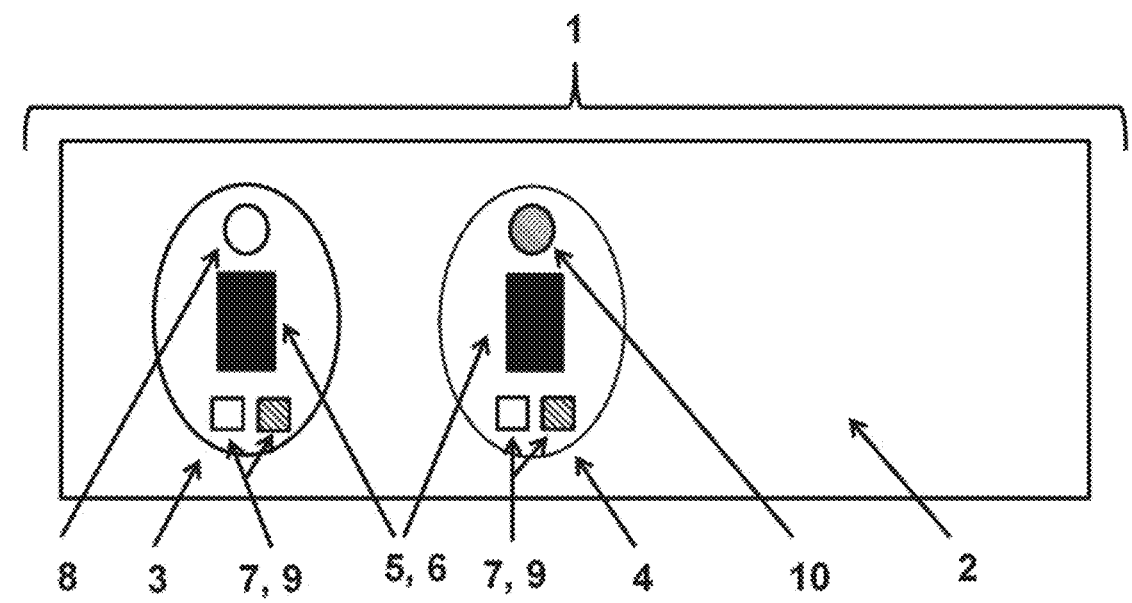
FIG. 1B shows a preferred embodiment of the present detection system containing in each area one donor control nucleic acid and two acceptor control nucleic acids.

FIG. 1A shows the detection system of the invention. Each area comprises one donor control nucleic acid and acceptor control nucleic acids whereas FIG. 1B shows a preferred embodiment of the present detection system containing in each area one donor control nucleic acid and two acceptor control nucleic acids.

Figure 2:
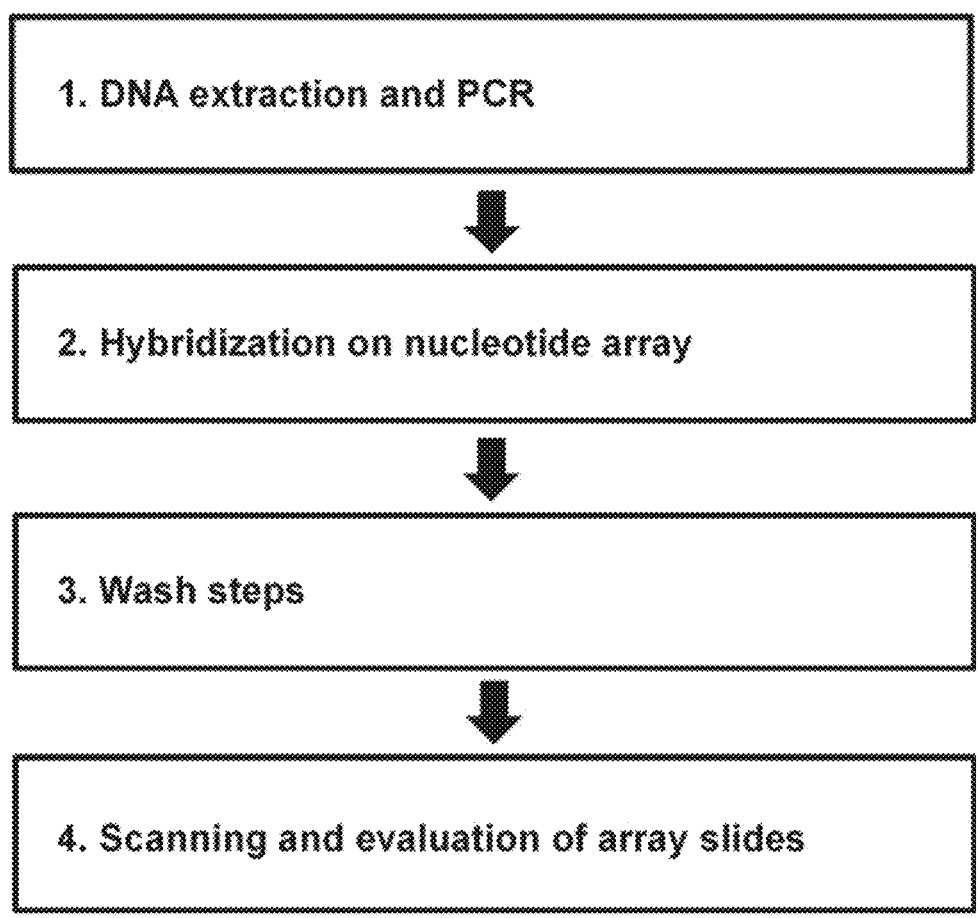
FIG. 2 shows the process flow for a nucleotide array comprising the steps of DNA extraction, PCR amplification, hybridization on the array, washing and array evaluation.

FIG. 2 shows the process flow for a nucleotide array comprising the steps of DNA extraction, PCR amplification, hybridization on the array, washing and array evaluation.

Figure 3:
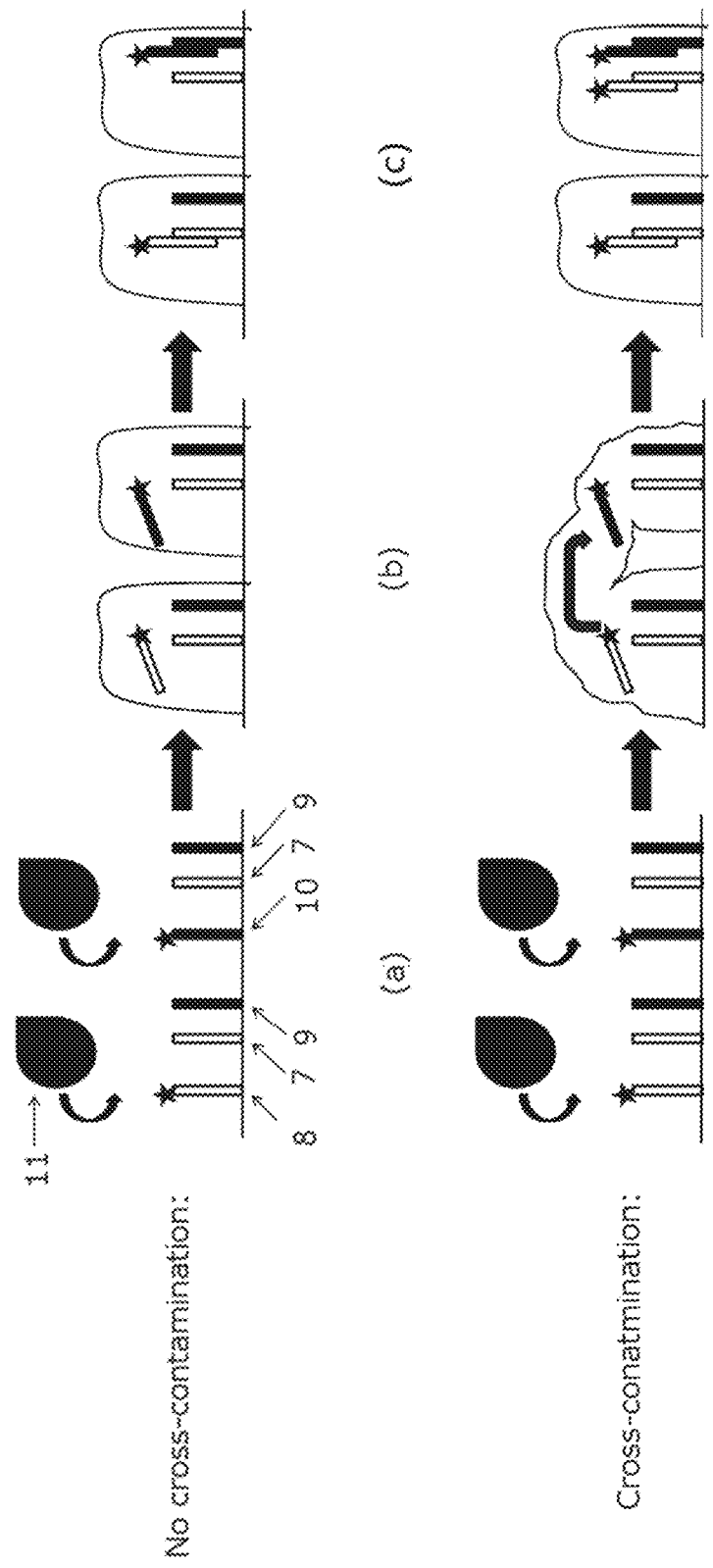
FIG. 3 shows the application of patient samples on the detection system of the invention. The upper row describes the application process without cross-contamination. The below pictures show the processes after a cross-contamination occurred in step (b). Step (a) depicts the application of a patient sample on the detection system. The donor control nucleic acid comprising a detectable label is dissolved in the patient sample (step (b)). Additionally, the below picture of step (b) shows that patient sample of the first area overflows into the second area. Step (c) shows that the donor control nucleic acids are bound to their corresponding acceptor control nucleic acids and that the signals caused by their labels allow their detection.

FIG. 3 shows the application of patient samples on the detection system of the invention. The upper row describes the application process without cross-contamination. The below pictures show the processes after a cross-contamination occurred in step (b). Step (a) depicts the application of a patient sample on the detection system. The donor control nucleic acid comprising a detectable label is dissolved in the patient sample (step (b)). Additionally, the below picture of step (b) shows that patient sample of the first area overflows into the second area. Step (c) shows that the donor control nucleic acids are bound to their corresponding acceptor control nucleic acids and that the signals caused by their labels allow their detection. FIG. 3 is based on a preferred embodiment of the invention, wherein each area contains one donor control nucleic acid and two acceptor control nucleic acids. The cross-contamination of the second area is indicated by the presence of two donor control nucleic acid signals.

FIG. 4 shows a preferred embodiment of the present invention, wherein the areas of the detection system are arranged to form horizontal and vertical rows. The white and the grey colors of the areas indicate that they alternatingly comprise the first and the second donor control nucleic acid.

FIG. 5 shows the results of nucleic acid detection using the detection system of the present invention. The results comprise non-contaminated controls and cross-contamination occurring during the application of the solution comprising the amplified HLA-B exons.

FIG. 6 shows the results of nucleic acid detection using the detection system of the present invention. The results comprise non-contaminated controls and cross-contamination occurring during a washing step after the solution comprising the nucleic acid of interest was already applied on the detection system.

Figure 7:
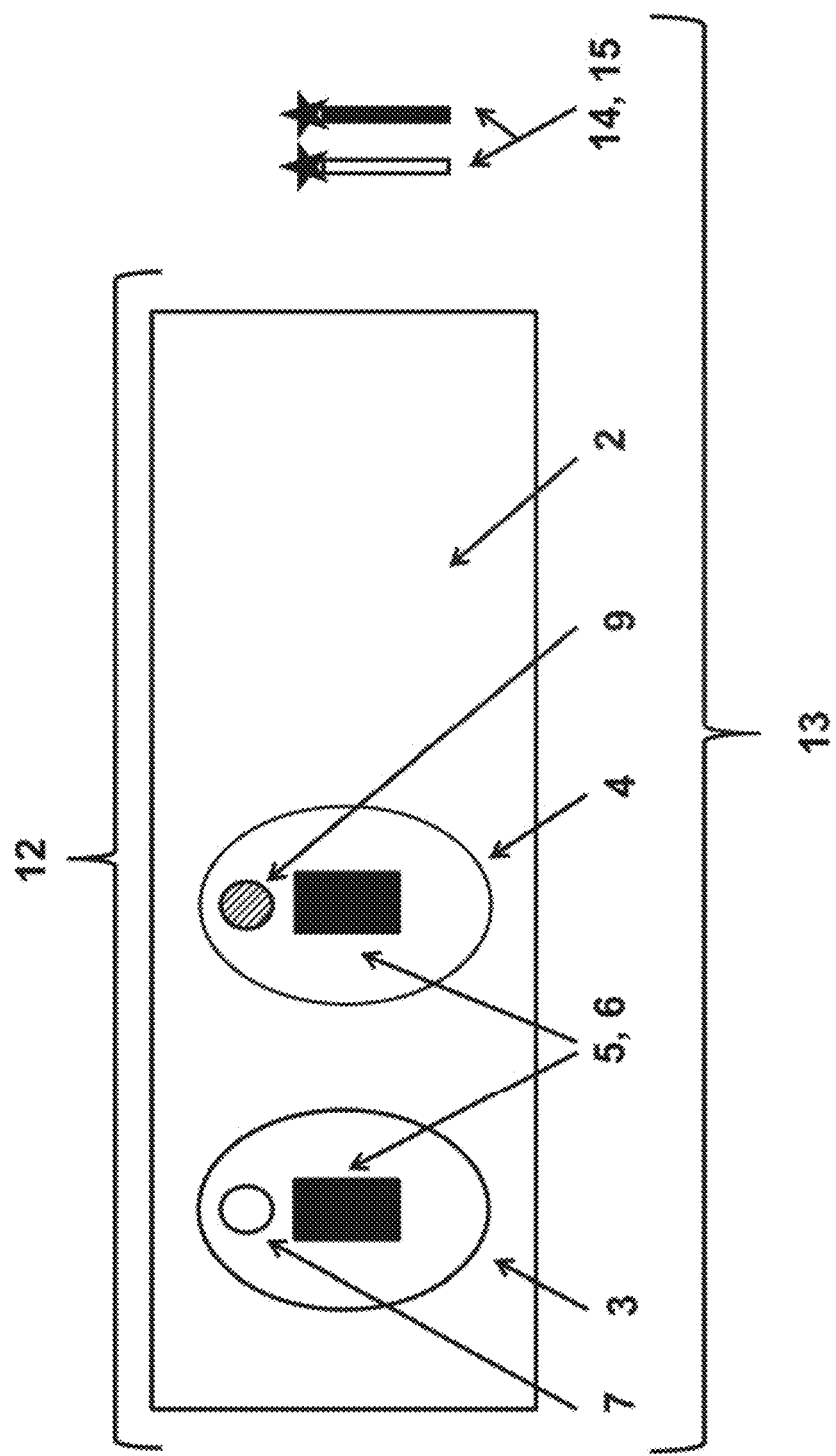
FIG. 7 shows the kit (13) of the invention including the nucleic acid or protein verification system (12) and the single-stranded donor control nucleic acids (14 and 15).

FIG. 7 shows the kit (13) of the invention including the nucleic acid or protein verification system (12) and the single-stranded donor control nucleic acids (14 and 15).

EXAMPLES

Embodiments

Preferably the cross-contamination detection system of the present invention consists of a glass slide which forms the carrier (2) of the system. In case nucleic acid cross-contamination is detected, such glass slide is preferably used after a nucleic acid extraction step from a patient sample and amplification by polymerase-chain-reaction (PCR) (cf. FIG. 2). The extraction step is usually carried out on a nucleic acid binding column, whereas the amplification step can be conducted on the 96-well plate.

In more preferred embodiments, the nucleic acid is DNA. The DNA of a patient sample can be extracted from other cellular parts and is subsequently amplified in a PCR using an appropriate set of primers. The amplified DNA is contacted with a glass slide containing several areas or fields with bound single-stranded DNA probes (5) which allow hybridization to the amplification products. During the PCR reaction the amplification products can be labeled by incorporating labeled nucleotides. Aside the single-stranded DNA probes, the area (3, 4) of the detection system (1) comprises a first single-stranded acceptor control nucleic acid (7) and a first single-stranded donor control nucleic acid (8). The glass slide comprises at least two areas (3, 4), however, preferred are three or five areas per glass slide.

Neighboring areas (3, 4) of the glass slide alternatingly comprise one of two different donor control nucleic acids (8, 10) and one of two different acceptor control nucleic acids (7, 9). The acceptor control nucleic acid and the donor control nucleic acid of alternating areas can bind to each other. Thus, the donor control nucleic acids (8, 10) will be solved after coming into contact with a liquid sample or a buffer comprising the sample (11) (cf. step (a) in FIG. 3). After the samples (11) are applied on the detection system (1), each area (3, 4) comprises an acceptor control nucleic acid (7, 9) covalently attached or attached by polycationic binding to the carrier and a solved donor control nucleic acid (8, 10) (cf. step (b) in FIG. 3). If no cross-contamination occurs, the donor control nucleic acid will be washed out and no signal can be detected (cf. step (c) in FIG. 3, upper row). However, in case of a (cross-)contamination (cf. step (b) in FIG. 3, lower row) the solved donor control nucleic acid (8) comes into contact with an acceptor control nucleic acid (9) of the neighbor area and both will bind to each other (cf. step (c) in FIG. 3, lower row). Even after washing steps the label of the donor control nucleic acid (8) can be detected.

FIGS. 1B and 3 show a preferred embodiment, wherein the area comprises both acceptor control nucleic acids (7, 9) The matching donor and acceptor control nucleic acid pair contained within the same area can be used as an internal area control.

FIG. 4 shows a further preferred embodiment, wherein the glass slide (2) comprises alternating areas (3, 4). In a more preferred embodiment, the glass slide (2) contains one row with five alternating areas resulting in an A-B-A-B-A scheme.

Experimental Data

FIG. 5 shows a set of data comprising microarray detection of exon 2 and exon 3 of the gene HLA-B in non-contaminated (cf. fields A and C) and cross-contaminated (cf. fields B and D) experiments. DNA was isolated from patient samples and amplified by PCR. The PCR amplifications products (exons 2 and 3 of HLA-B gene) are applied on a carrier (2) containing areas (3, 4) as fields A, B, C and D containing the fields A, B, C and D. The fields A, B, C and D all contain HLA-B exon 2 and 3 probes. However, only the samples A and C are positive for the HLA-B27 exon 2 and HLA-B27 exon 3. Further, all fields contain both acceptor control nucleic acids. The fields A and C comprise the first donor control nucleic acid, whereas the fields B and D comprise the second donor control nucleic acid. The results for the detection of the first donor control nucleic acid are presented in the row "CC-I". The results for the detection of the second donor control nucleic acid are presented in the row "CC-II". All experiments have been carried out based on parallel measurements.

As expected, for the control fields A and C only signals for the first donor control nucleic acid (CC-I) can be measured. No detection of the second donor control nucleic acid (CC-II) can be observed. Fields B and D are intentionally cross-contaminated with the first solutions applied on fields A and C (field B was specifically contaminated with the solution of field A and field D was specifically contaminated with the solution of field C). Consistently, the fields B and D do not only show a signal of the second donor control nucleic acid (CC-II) but also of the first donor control nucleic acid (CC-I) which results from the cross-contamination with the solutions applied on fields A and C. In addition, unclear signals for the B27 exon 2 and B27 exon 3 can be measured.

The experiments of FIG. 6 are similar to the experiments of FIG. 5 with the exception that the cross-contamination of fields B and D did not occur during application with the first solution but during a later washing step. Consistently, the cross-contamination signals in fields B and D (CC-I) are weaker compared to the cross-contamination signals of FIG. 5. Nonetheless, the cross-contamination signals of FIG. 6 can be clearly identified as positive signals. Signals of 500 units or more are considered positive signals for the cross-contamination system. The CC-I signals for field B are over 1000 units, whereas the CC-I signals for field D are over 1500 units. Thus, the cross-contamination system of the present invention is able to detect cross-contaminations occurring when a first solution is applied on the control nucleic acids as well as cross-contaminations occurring in later washing steps.

All documents cited herein, are hereby incorporated by reference in their entirety.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the embodiments disclosed herein. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following embodiments.

LIST OF REFERENCE SIGNS 1 nucleic acid or protein detection system
2 carrier
3 first area
4 second area
5 single-stranded nucleic acids
6 proteins
7 first single-stranded acceptor control nucleic acid
8 first single-stranded donor control nucleic acid
9 second single-stranded acceptor control nucleic acid
10 second single-stranded donor control nucleic acid
11 patient sample
12 nucleic acid or protein verification system
13 kit
14 first single-stranded donor control nucleic acid
15 second single-stranded donor control nucleic acid

The invention claimed is:
1. A nucleic acid or peptide detection system, comprising:
a carrier with at least two areas;
wherein a first of the at least two areas comprises
single-stranded nucleic acids covalently attached to the carrier for detection of nucleic acids of interest or peptides covalently attached to the carrier for detection of peptides of interest;
a first single-stranded acceptor control nucleic acid covalently attached to the carrier or attached by polycationic binding to the carrier; and
a first single-stranded donor control nucleic acid non-covalently attached to the carrier, the first single-stranded donor control nucleic acid comprising a detectable label;
wherein a second of the at least two areas comprises the single-stranded nucleic acids covalently attached to the carrier for detection of nucleic acids of interest or peptides covalently attached to the carrier for detection of peptides of interest;
a second single-stranded acceptor control nucleic acid covalently attached to the carrier or attached by polycationic binding to the carrier; and
a second single-stranded donor control nucleic acid non-covalently attached to the carrier, the second single-stranded donor control nucleic acid comprising a detectable label;
wherein the second single-stranded donor control nucleic acid is able to hybridize under suitable conditions with the first single-stranded acceptor control nucleic acid; and
the first single-stranded donor control nucleic acid is able to hybridize under suitable conditions with the second single-stranded acceptor control nucleic acid;
wherein the first single-stranded acceptor control nucleic acid is at least 80% complementary to the second single-stranded donor control nucleic acid over a stretch of at least 10 nucleotides; and/or
the second single-stranded acceptor control nucleic acid is at least 80% complementary to the first single-stranded donor control nucleic acid over a stretch of at least 10 nucleotides.

2. The nucleic acid or peptide detection system according to claim 1, wherein
the first of the at least two areas additionally comprises the second single-stranded acceptor control nucleic acid covalently attached to the carrier or attached by polycationic binding to the carrier; and
the second of the at least two areas additionally comprises the first single-stranded acceptor control nucleic acid covalently attached or attached by polycationic binding to the carrier.

3. The nucleic acid or peptide detection system according to claim 1, wherein
a) the single-stranded nucleic acids and the first single-stranded acceptor control nucleic acid and the second single-stranded acceptor control nucleic acid are spatially separated;
b) the peptides covalently attached to the carrier and the first single-stranded acceptor control nucleic acid and the second single-stranded acceptor control nucleic acid are spatially separated; or
c) the first single-stranded acceptor control nucleic acid in the first of the at least two areas and the second single-stranded acceptor control nucleic acid in the second of the at least two areas are spatially separated.

4. The nucleic acid or peptide detection system according to claim 1, wherein the first single-stranded donor control nucleic acid and the second single-stranded donor control nucleic acid are dried up on the carrier.

5. The nucleic acid or peptide detection system according to claim 1, wherein the detection label of the first single-stranded donor control nucleic acid and the second single-stranded donor control nucleic acid is a dye.

6. The nucleic acid or peptide detection system according to claim 5, wherein the dye is selected from the group consisting of cyanine derivatives, fluorescein, fluorescein isothiocyanate (FITC), 6-FAM phosphoramidite, 6-JOE, rhodamines, 5-TAMRA, ROX, and Texas Red.

7. The nucleic acid or peptide detection system according to claim 1, wherein each of the single-stranded nucleic acids, the first single-stranded acceptor control nucleic acid, the second single-stranded acceptor control nucleic acid, the first single-stranded donor control nucleic acid, and the second single-stranded donor control nucleic acid has a length of 10 to 100 nucleotides.

8. The nucleic acid or peptide detection system according to claim 1, wherein the carrier material is plastic, glass, or metal.

9. A method for detecting a nucleic acid or a peptide of interest, comprising:
contacting the nucleic acid or peptide of interest with the nucleic acid or peptide detection system according to claim 1.

10. A nucleic acid or peptide detection system comprising:
a carrier with at least two areas;
wherein a first of the at least two areas comprises
single-stranded nucleic acids covalently attached to the carrier for detection of nucleic acids of interest or peptides covalently attached to the carrier for detection of peptides of interest;
a first single-stranded acceptor control nucleic acid covalently attached to the carrier or attached by polycationic binding to the carrier; and
a first single-stranded donor control nucleic acid non-covalently attached to the carrier, the first single-stranded donor control nucleic acid comprising a detectable label;
wherein a second of the at least two areas comprises
the single-stranded nucleic acids covalently attached to the carrier for detection of nucleic acids of interest or peptides covalently attached to the carrier for detection of peptides of interest;
a second single-stranded acceptor control nucleic acid covalently attached to the carrier or attached by polycationic binding to the carrier; and
a second single-stranded donor control nucleic acid non-covalently attached to the carrier, the second single-stranded donor control nucleic acid comprising a detectable label:
wherein the second single-stranded donor control nucleic acid is able to hybridize under suitable conditions with the first single-stranded acceptor control nucleic acid; and
the first single-stranded donor control nucleic acid is able to hybridize under suitable conditions with the second single-stranded acceptor control nucleic acid;
wherein the at least two areas are arranged to form at least one row.

11. The nucleic acid or peptide detection system according to claim 10, wherein the at least two areas alternatingly comprise (i) the first single-stranded acceptor control nucleic acid and the first single-stranded donor control nucleic acid; and (ii) the second single-stranded acceptor control nucleic acid and the second single-stranded donor control nucleic acid.

12. A kit, comprising:
(I) a nucleic acid or protein verification system comprising a carrier with at least two areas,
wherein a first of the at least two areas comprises
single-stranded nucleic acids covalently attached to the carrier for detection of nucleic acids of interest or peptides covalently attached to the carrier for detection of peptides of interest;
a first single-stranded acceptor control nucleic acid covalently attached to the carrier or attached by polycationic binding to the carrier; and
wherein a second of the at least two areas comprises the single-stranded nucleic acids covalently attached to the carrier for detection of nucleic acids of interest or peptides covalently attached to the carrier for detection of peptides of interest;
a second single-stranded acceptor control nucleic acid covalently attached to the carrier or attached by polycationic binding to the carrier; and
(II) a first single-stranded donor control nucleic acid comprising a detectable label and a second single-stranded donor control nucleic acid comprising a detectable label;
wherein the second single-stranded donor control nucleic acid is able to hybridize under suitable conditions with the first single-stranded acceptor control nucleic acid; and
the first single-stranded donor control nucleic acid is able to hybridize under suitable conditions with the second single-stranded acceptor control nucleic acid;
wherein the first single-stranded acceptor control nucleic acid is at least 80% complementary to the second single-stranded donor control nucleic acid over a stretch of at least 10 nucleotides; and/or
the second single-stranded acceptor control nucleic acid is at least 80% complementary to the first single-stranded donor control nucleic acid over a stretch of at least 10 nucleotides.

13. The kit according to claim 12, comprising sample tubes, wherein the first single-stranded donor control nucleic acid and the second single-stranded donor control nucleic acid are separately and non-covalently attached to the sample tubes.

14. A method for detecting a nucleic acid or a peptide of interest, comprising:
contacting the nucleic acid or peptide of interest with the nucleic acid or protein verification system of the kit according to claim 12 and the first single-stranded donor-control nucleic acid and the second single-stranded donor control nucleic acid.

* * * * *